United States Patent [19]
Wada et al.

[11] Patent Number: 5,831,060
[45] Date of Patent: Nov. 3, 1998

[54] CPC GENE FOR REGULATING INITIATION OF ROOT HAIR FORMATION FOR ARABIDOPSIS (THALIANA) AND TRANSGENIC (ARABIDOPSIS), PLANT OVEREXPRESSING THE CPC GENE

[75] Inventors: Takuji Wada, Osaka; Kiyotaka Okada, Kyoto, both of Japan

[73] Assignee: Biomolecular Engineering Research Institute, Suita, Japan

[21] Appl. No.: 814,030

[22] Filed: Mar. 10, 1997

[30] Foreign Application Priority Data

Apr. 29, 1996 [JP] Japan .................................. 8-107409
Feb. 13, 1997 [JP] Japan .................................. 9-028877

[51] Int. Cl.$^6$ .......................... A01H 1/06; C07K 14/415; C12N 15/29
[52] U.S. Cl. ...................... 536/23.6; 536/23.1; 800/200; 800/205; 435/69.1; 435/419; 530/300
[58] Field of Search ..................... 435/69.1, 419; 530/300; 536/23.6, 23.1; 800/205, 200

[56] References Cited

FOREIGN PATENT DOCUMENTS

WO 93 20206
    A  10/1993  WIPO.
WO 94 10831
    A  5/1994  WIPO.

OTHER PUBLICATIONS

D.G. Oppenheimer, et al., "A myb Gene Required for Leaf Trichome Differentiation in Arabidopsis is Expressed in Stipules". Cell vol. 67, 1 Nov. 1991, pp. 483–493.
K.C. Cone et al., "Role of the Regulatory Gene pI in the Photocontrol of Maize Anthocyanin Pigmentation", The Plant Cell, vol. 5, 1993, pp. 1807–1816.
J.W. Schiefelbein, et al., "Genetic Control of Root Hair Development in Arabidopsis Thaliana", The Plant Cell, vol. 2, 1990, pp. 235–243.
K.C. Cone et al., "Role of the Regulatory Gene pI in the Photocontrol of Maize Anthocyanin Pigmentation", Embl Sequence Data Library, 1 Nov. 1996, Heidelberg, Germany.
J.D. Masucci et al., "Hormones Act Downstream of TTG and GL2 to Promote Root Hair Outgrowth During Epidermis Development in the Arabidopsis Root", The Plant Cell, vol. 8, Sep. 1996, pp. 1505–1517.
European Search Report dated Oct. 13, 1997.

*Primary Examiner*—Ponnathapura Achutamurthy
*Assistant Examiner*—Phuong T. Bui
*Attorney, Agent, or Firm*—Finnegan, Henderson, Farabow, Garrett & Dunner, L.L.P.

[57] ABSTRACT

Disclosed are a CPC gene coding for the amino acid sequence of SEQ ID NO:1 or an amino acid sequence substantially identical with the amino acid sequence of SEQ ID NO:1 and plants having said gene introduced into them. Novel plants with an increased number of root hairs can be obtained by use of said gene.

2 Claims, 6 Drawing Sheets

WILD TYPE

CPC GENE FOR REGULATING INITIATION OF ROOT HAIR FORMATION FOR ARABIDOPSIS (THALIANA) AND TRANSGENIC (ARABIDOPSIS), PLANT OVEREXPRESSING THE CPC GENE

FIELD OF THE INVENTION

The present invention relates to a novel gene for promoting the formation of plant root hairs, as well as transgenic plants overexpressing this gene.

BACKGROUND OF THE INVENTION

Known mutants on plant root hairs include those with an increased number of root hairs, such as ttg (transparent test glabra), gl2 (glabrous2) (Galway M. E. et al., Dev. Biol. 166 740–754 (1994), Rerie W. G. et al., Genes & Development, 8 1388–1399 (1994)) and those with root hairs of abnormal shapes, such as rhd1, rhd2, rhd3 and rhd4 (Schiefelbein, J. & Somerville, C., Plant Cell 2 235–243 (1990)). Known mutants with a less number of root hairs include rhd6, and these mutants are complemented with a plant hormone such as auxin (Masucci, J. D. & Schiefelbein, J. W., Plant Physiol. 106 1335–1346 (1994)), but a mutant not complimented with a plant hormone such as auxin, that is, a mutant having abnormality in its signal transmission system for making root hairs, was not known.

SUMMARY OF THE INVENTION

If a mutant coming to have a less number of root hairs due to abnormality in the signal transmission system for making root hairs can be separated, a gene involved in forming root hairs could be identified by examining the site with this abnormality.

The present invention was made under these technical backgrounds, and the object of the present invention is to isolate a novel gene for promoting the formation of plant root hairs and to provide transgenic plants having the gene introduced into them.

As a result of their eager research, the present inventor successfully isolated mutated Arabidopsis with a less number of root hairs, cloned a gene involved in this mutation in said plant, further introduced the gene into wild-type Arabidopsis to express it, and on the basis of these findings they completed the present invention.

That is, the present invention is a novel gene coding for the amino acid sequence of SEQ ID NO:1 or an amino acid sequence substantially identical with the amino acid sequence of SEQ ID NO:1.

In addition, the present invention is plants having said gene introduced into them.

DETAILED DESCRIPTION OF THE INVENTION

Figure 1:
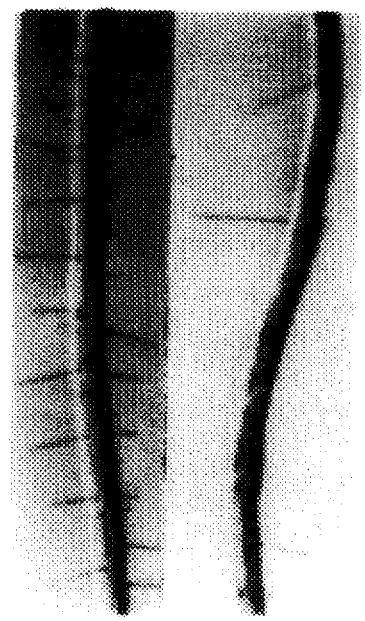
FIG. 1 is a photograph of a root of caprice.

Hereinafter, the present invention is described in detail.

The gene of the present invention codes the amino acid sequence of SEQ ID NO:1 or an amino acid sequence substantially identical with the amino acid sequence of SEQ ID NO:1. The "amino acid sequence substantially identical with the amino acid sequence of SEQ ID NO:1" herein used refers to an amino acid sequence represented by SEQ ID NO:1 with some amino acids being deleted, replaced, added etc. and with the same working effect as that of the amino acid sequence of SEQ ID NO:1, i.e. having the effect of promoting the formation of plant root hairs. To cause some amino acids to be deleted, replaced, added etc., techniques known in the state of art, for example site-directed mutagenesis (Nucleic Acid Research, Vol. 10, No. 20, pp. 6487–6500 (1982)), can be used.

The gene of the present invention works for promoting formation of root hairs. This can be inferred from the fact that a mutant with this gene destroyed has a less number of root hairs. Although known mutants with a less number of root hairs include rhd6 as mentioned in "Background of the Invention", a mutant originating in the gene of the present invention differs from rhd6 in that it is not compensated with a plant hormone. Therefore, this mutant is not known. The present inventors named this mutant "caprice" because it produces root hairs in some case but not in other case, and a gene involved in this mutation was designated "CPC".

The CPC gene can be cloned for example in the following manner. Fist, genomic DNA isolated from Arabidopsis was cleaved with a suitable restriction enzyme, the fragmented DNA is linked to a suitable vector, and this recombinant vector is transformed into a microorganism as a host to prepare a genomic DNA library. Isolation of the DNA can be carried out using cesium chloride and ethidium bromide in a usual manner. It is not necessary for the restriction enzyme to be special. For example, Sau3AI etc. can be used. It is not necessary for the vector to be special as well. For example, λ-DASH II etc. can be used. The microorganism to be used as a host can be selected depending on the vector used. For example, if λ-DASH II is used as the vector, E. coli XL-1 Blue MRA(P2) etc. can be used.

Then, the above genomic DNA library is screened. The probe used is DNA located near T-DNA in the mutant caprice. Because the CPC gene of the caprice has been destroyed by inserting T-DNA, DNA near T-DNA contains a part of the CPC gene.

The vector is removed from the positive clone thus selected with the above probe, and a DNA fragment obtained from this vector is used as a probe for screening of a cDNA library. This cDNA library can be prepared in a usual manner. That is, total RNA is isolated from the plant, then oligo(dT) etc. is used to isolate mRNA from the total RNA, and the mRNA is used to prepare cDNA by reverse transcriptase. The cDNA is linked to a suitable vector, and the resulting recombinant vector is transformed into microorganisms as a host. The recombinant vector contained in the positive clone selected by screening contains the CPC gene of the present invention.

The expression of the CPC gene in plants can be effected by inserting the CPC gene into a suitable plant expression vector and then introducing the resulting recombinant vector into plants. The plant expression vector herein used is not limited if it has a promoter and a marker gene capable of functioning in plants. Preferably, the vector has a 35S promoter from cauliflower mosaic virus, capable of functioning in a wide variety of plants. Such vectors include pBI121 (Clontech) etc. in addition to pMAT137-Hm used in the Examples. To introduce the vector into plants, Agrobacterium is preferably used, but other means such as electroporation, a particle gun etc. may also be used. Plants used to express the CPC gene include, but are not limited to, rose, tobacco, tomato, rice, maize, petunia, Brassica etc., and these plants are preferably used.

The CPC gene of the present invention functions as follows:

(1) It works for promoting the formation of root hairs for plants. Therefore, a plant having more root hairs than usual one can be produced by the introduction and excessive expression of the CPC gene. Such plants are expected to be more resistant to dryness because of their high ability to absorb water.

(2) It works for reducing trichomes in leaves and stems. Therefore, a plant such as rose will be able to have less thorns by the introduction and excessive expression of the CPC gene.

(3) It works for hastening the flowing time of a plant. Therefore, it is expected that a plant will flower earlier by the introduction and excessive expression of the CPC gene.

(4) It works for reducing an accumulation of anthocyanin in leaves. That is, when Arabidopsis is grown at a low temperature of about 16° C., its leaves etc. will turn reddish purple because of the accumulation of anthocyanin pigments. However, anthocyanin is hard to accumulate in a plant where the CPC gene is excessively expressed, so the color of its leaves will remain green even if grown at 16° C. Because a red color in flowers is generally caused by anthocyanin type pigments, it is expected that a plant with colored flowers can change the color of its flowers by the introduction and excessive expression of the CPC gene.

EFFECT OF THE INVENTION

The present invention provides the CPC gene which is a novel gene for promoting the formation of root hairs for plants. The introduction and expression of this gene in plants promotes formation of root hairs while trichomes in leaves and stems can be decreased.

EMBODIMENT FOR CARRYING OUT THE INVENTION

Example 1
Production of Transgenic Plants

Seeds from *Arabidopsis thaliana* (variety:. Wassilewskija [WS]) were sterilized and seeded in an agar medium. During two to four days after seeding, the seeds were cultivated in the dark to break dormancy, to attain uniform germination and to flower earlier. Thereafter, they were cultivated at 22° C. under continuous lighting. For sterilization, the seeds were placed in a 1.5 ml Eppendorf tube, followed by adding 0.5 ml sterilized distilled water containing 10% Highter™ (Kao Corporation) and 0.02% Triton X-100. The seeds in the tube were stirred with Boltex™, then left at room temperature for 3 to 5 minutes, and washed 5 times with sterilized distilled water. As the agar medium, a nutrient salt solution for *Arabidopsis thaliana* (985 ml distilled water or deionized water, 5 ml of 1 M KNO$_3$, 2 ml of 1M MgSO$_4$, 2 ml of 1M Ca(NO$_3$)2, 2.5 ml of 20 mM Fe-EDTA, 1 ml trace element solution, 2.5 ml K-PO$_4$ buffer (pH 5.5)) (Hideaki Shiraishi et al., "Gendai Kagaku" (Modern Chemistry), Extra Edition 20, Plant Biotechnology II, page 38, (1991)) was diluted with an equal volume of distilled water and then agar powder (guaranteed reagent, Nakarai K. K.) was added to it at 1.5% concentration, and it was autoclaved and poured into a vessel to be solidified. Because this concentration of an agar medium permits the Arabidopsis to grow its roots on the agar surface without entering into the medium, the form of the roots can be easily examined in the subsequent step. The light source used was a commercial two 40 kw white fluorescent lamps and one fluorescent lamp for plant growth (Homolux™, National) and the seeds were irradiated with light about 30 cm apart from the light source. The brightness of this light source was about 3000 lux.

Three weeks after seeding, Agrobacterium was inoculated onto 40 Arabidopsis seedlings. The inoculation of Agrobacterium was carried out by cutting a floral stem of Arabidopsis to infect it with Agrobacterium, according to a modification of the in planta method (Chang et al., Plant J., 5 551–558 (1994)). The Agrobacterium used was *Agrobacterium tumefaciens* C58C1Rif obtained from Velten, J et al. (Velten, J. and Schell, J, Nucl. Acids Res. 13, 6981–6998 (1985)). This strain contained an intermediary system vector pGV3850HPT in which a hygromycin transferage gene was located as a plant selective marker between its right and left borders downstream of a 35S promoter derived from cauliflower mosaic virus.

After inoculation of Agrobacterium, the Arabidopsis was planted in culture soil consisting of a mixture of vermiculite and perlite (1:1). 1.5 to 2 months after planting, their seeds (T2 seeds) were harvested. The seeds were sterilized in the same manner as above, seeded and grown in a hygromycin-containing medium (mixed salt for 1×Ganborg B5 medium, 1% sucrose, 0.8% agar, 10 mg/l hygromycin B) and those with resistant to hygromycin were picked up and planted in culture soil. The culture soil was the same as described above. 1.5 to 2 months after planting, their seeds (T3 seeds), obtained by self-pollinated, were harvested.

Example 2
Screening of Root Mutant

The T3 seeds obtained in Example 1 were sterilized, seeded and cultivated in an agar medium. The sterilization method and the agar medium were the same as described above. The agar medium was placed in a transparent plastic vessel so that the form of roots could be easily examined (No. 2 rectangular vessel [14×10 cm], Eiken Kizai K. K.).

The form of roots was examined with transmitted light under a stereoscopic microscope OLYMPUS SZH-IDDL. Roots from about 300 lines of transgenic Arabidopsis were examined, from which one mutant line with a less number of roots was isolated. The roots of this mutant are shown in FIG. 1. The mutant is shown in the right and the wild-type in the left. As is evident from FIG. 1, this mutant has a less number of root hairs than that of the wild-type, but there is no difference between the two in the length of their root hairs.

Example 3
Genetic Investigation of Caprice

To examine the mutation in caprice genetically, caprice was backcrossed with the WS strain i.e. a wild-type strain of Arabidopsis. The crossing of caprice with the WS strain was conducted as described by Okada et al., as follows. A caprice bud whose stamen anther did not dehisce was opened with a pair of tweezers (Dumoxel No. 5, available from A Dumonte Fils), and all except for the pistil were removed and the remaining pistil was used as a female parent. A pair of tweezers and fingertips were previously sterilized with 95% ethanol to prevent contamination with pollen. About 2 days after this treatment, the stigma of the caprice pistil was confirmed to have no pollen attached to it, and then pollens collected from a flower of the WS strain were put to the stigma of the caprice pistil. This backcross gave fourteen F1 plants. They all had the phenotype of the wild-type.

All the 14 plants were then self-pollinated to give F2 progeny. In the F2 progeny, 257 plants had the phenotype of the wild-type and 67 plants had the phenotype of the caprice. Because this F2 generation showed a 3:1 ratio of the wild-type to caprice phenotype, it was estimated that caprice resulted from a mutation on one recessive allele.

Example 4
Isolation of Genomic DNA from Transgenic Arabidopsis

The isolation of genomic DNA from Arabidopsis was carried out as described by Doyle and Doyle (Isolation of plant DNA from fresh tissue, Focus 12, 13–15 (1990)), as follows:

Three to four weeks after germination, 2 to 3 developed rosette leaves were removed from Arabidopsis (caprice) with a pair of tweezers, placed in 1.5 ml Eppendorf tube, and disrupted with a pellet pestle (Kontes) in 200 ml CTAB buffer (3% cetylmethylammonium bromide, 1.4M NaCl, 0.2% 2-mercaptoethanol, 20 mM EDTA, 100 mM Tris-HCl (pH 8.0)). Additional 300 ml CTAB buffer was added to it and kept at 60° C. for 30 minutes. Thereafter, chloroform was added to it, and the supernatant was recovered and precipitated with isopropanol. After RNase treatment, phenol treatment, and ethanol precipitation, the sample was dissolved in 10 to 25 ml Tris-EDTA (10 mM Tris-HCl (pH 8.0), 1 mM EDTA-$Na_2$ (pH 8.0)).

Example 5
Southern Analysis of Genomic DNA from Transgenic Arabidopsis

The genomic DNA from Arabidopsis (caprice) obtained in Example 4 was analyzed by Southern blotting. The Southern blotting was carried out as described in Current Protocol (Ausbel et al. (1987)).

0.5 to 1 g of the DNA obtained from caprice was cleaved with HindIII and subjected to agarose electrophoresis. After electrophoresis, the gel was immersed in 0.25M hydrochloric acid and then shaken for 10 minutes. The gel was then shaken once in a denaturant solution (1.5M NaCl, 0.5M NaOH) for 30 minutes and twice in a neutralization solution (1.5M NaCl, 0.5M Tris-HCl pH 7.2, 1 mM EDTA) for 20 minutes. After shaking, Hybond N (Amersham) was placed on the gel and irradiated with UV rays from UV stratalinker 2400 (Stratagene) to fix the DNA on it.

Separately, a probe was prepared by removing a left border region from pGV3850HPT and labeling it with [α-32P]dCTP by a random primer labeling kit (Takara Shuzo Co., Ltd.). The above Hybond N was immersed overnight in a hybridization solution containing this probe (5×SSC, 0.1% N-lauroylsarcosine, 0.02% SDS, 1% blocking reagent (Boehringer)) for hybridization. As a result, only one single band appeared in the position of 4.9 kb, similar to FIG. 3 as described below.

Example 6
Isolation of Genomic DNA Near T-DNA from Arabidopsis

Because it was estimated from Example 5 that only one T-DNA was inserted into only one position in the genomic DNA of caprice, isolation of genomic DNA near the T-DNA was attempted by the inverse PCR technique. The inverse PCR technique followed the method of Deng et al. (Cell 71 791–801 (1992)).

The caprice DNA obtained in Example 4 was cleaved with HindIII (Takara Shuzo Co., Ltd.) and then electrophoresed in 1% agarose gel, and a gel portion containing DNA with 4 to 6 kb was cut off from from the gel, and DNA was extracted. To this DNA was added DNA ligase (Takara Shuzo Co., Ltd.) for self-ligation, and PCR was carried out with the following primers (LB1 and LB2) to amplify the left border in the outward direction.

LB1: CAC GCC ATC GAT GTA ATA ATT GTC ATT GTC ATT AGA TTG T SEQ ID NO:3

LB2: GAG CTA TTG GCA CAC GAA GAA TGG T SEQ ID NO:4

PCR was carried out in 35 cycles each consisting of reactions at 94° C.×30 seconds, 60° C.×30 seconds, and 72° C.×30 seconds in GeneAmp PCR system 9600 (Perkin Elmer). As a result, an about 2 kb fragment was amplified.

Figure 2:
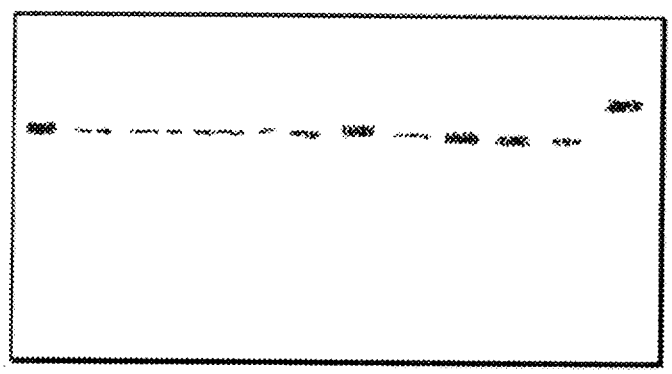
FIG. 2 shows Southern blotting of caprice and the wild-type.

Then, this fragment was used as a probe to isolate DNA from caprice and the wild-type WS strain respectively, and the DNA was cleaved with HindIII and then subjected to Southern blotting. The Southern blotting was carried out in the same manner as in Example 5. The result is shown in FIG. 2. In this photograph, "wt" is the wild-type WS, and 1–11 are caprice. As shown in FIG. 2, the DNA from caprice showed a band at the position of 4.9 kb, similar to the case where the left border was used as a probe, while the DNA from the wild-type WS showed a band at the position of about 11 kb.

Figure 3:
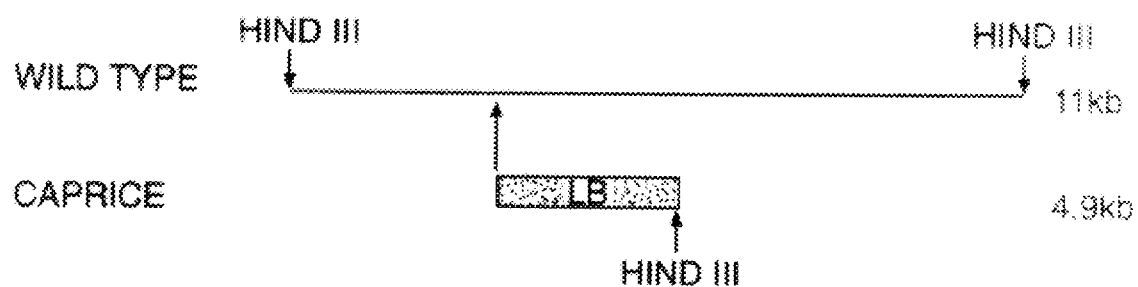
FIG. 3 shows the HindIII cleavage sites of caprice and the wild-type.

This difference in the band positions between the 2 strains is attributable to the presence of a HindIII cleavage site in the left border which was inserted into the genomic DNA of caprice. As shown in FIG. 3, the wild-type DNA into which the left border was not inserted is cleaved at only the 2 cleavage sites inherent in its genomic DNA. On the other hand, the caprice DNA into which the left border was inserted is cleaved further at the cleavage site located in the left border, resulting in the shorter fragment.

Example 7
Cloning of the CPC Gene

The part of the WS strain over the ground was collected and the tissues were frozen in liquid nitrogen and crushed in a mortar, and DNA was isolated with cesium chloride and ethidium bromide. The isolated DNA was partially digested with Sau3AI (Takara Shuzo Co., Ltd.) and subjected to sucrose density-gradient centrifugation. Fractions containing 15 to 20 kb fragments were collected and this genomic DNA was then ligated to $_\gamma$-DASH II previously cleaved with BamHI (Takara Shuzo Co., Ltd.). The resulting recombinant vector was subjected to invitro packaging with Gigapack II Packaging Extract (Stratagene). About 100,000 phages thus packaged were scattered on an LB plate (1 L deionized water, 10 g Bacto-trypton, 5 g Bacto-yeast, 10 g NaCl, and 1.2% agar) to construct a genomic library of Arabidopsis. This library was then screened where the about 2 kb DNA fragment isolated in Example 6 was used as a probe. As a result, 4 positive clones were isolated. These phage clones were cleaved with EcoRI and XbaI and then subjected to Southern blotting with the above 2 kb DNA fragment as a probe. Out of the fragments with which the probe was hybridized, 3 fragments, that is, 4.4 kb fragment cleaved with EcoRI and 7.3 kb and 5 kb fragments cleaved with XbaI, were cloned in plasmid vector Bluescript SK+ (Stratagene).

Then, total RNA was isolated as described in Current Protocol from roots of Arabidopsis. 2 to 4 g of root tissues from Arabidopsis were frozen in liquid nitrogen and crushed in a mortar. It was then stirred in a buffer containing guanidine thiocyanate and ultracentrifuged (22,000 r.p.m. for 16 hours) to precipitate the RNA. The precipitate was suspended in a solution containing 5 mM EDTA, 0.5 % sarcosyl, and 5% 2-mercaptoethanol to recover the RNA. From the total RNA thus obtained, poly(A)$^+$ RNA was recovered using Oligotex-dT30 [Super]™ (Nippon Roche K. K.). The poly(A)$^+$ RNA could be recovered in the range of 0.5 to 1% of the total RNA. An oligo-dT primer with an XhoI cleavage site at the 3-terminal was annealed to the recovered poly(A)$^+$ RNA (5g g), and reverse transcriptase (Strata Script reverse transcriptase, produced by Stratagene) was used to synthesize double-stranded cDNA from it. Because this double-stranded cDNA had the EcoRI and XhoI cleavage sites at the 5'- and 3'-terminals respectively, it was cloned in ZAPII vector (Stratagene) previously cleaved with EcoRI and XhoI. The resulting recombinant vector was subjected to in vitro packaging with Gigapack II Packaging Extract (Stratagene). About 300,000 packaged phages were scattered on an LB plate containing $E.$ $coli$ XLI-Blue MRF' to prepare a cDNA library of Arabidopsis, and this library was screened with the above 5 kb fragment cleaved with XbaI. As a result, 4 positive clones were separated. The longest cDNA contained in the resulting clones was sequenced. This sequence reaction was carried out using Dye primer cycle sequencing FS kit and Dye terminator cycle sequencing FS ready reaction kit (Perkin Elmer), and the nucleotide sequence was determined with a fluorescent automatic sequencer (Model 370A, ABI). The sequence thus determined is shown in SEQ ID NO:2. The length of the DNA was 584 bp, and the translation of its longest ORF gave 94 amino acids with a molecular weight of 11 kD. As shown in SEQ ID NO:2, two termination codons were present upstream of the origin of replication.

Example 8

Preparation of Plants with Excessive Expression of the CPC Gene pMAT137-Hm (obtained from Dr. Ken Matsuoka, Applied Biological Chemistry, Agricultural Department, Nagoya University, Japan; Matsuoka, K. and Nakamura, K., Proc. Natl. Acad. Sci. USA 88, 834–838 (1991)) was cleaved with restriction enzymes XbaI (Takara Shuzo Co., Ltd.) and KpnI (Takara Shuzo Co., Ltd.). In this vector, three 35S promoters from cauliflower mosaic virus are linked in tandem and an arbitrary gene can be cloned in a multicloning site located downstream of the promoters. Further, a hygromycin transferase gene is linked as a drug resistant gene to another 35S promoter and can function as a drug resistant gene in $E.$ $coli$, Agrobacterium, and plants.

The CPC gene cloned in Bluescript SK+vector (Stratagene) was cleaved in the same manner as above with restriction enzymes XbaI (Takara Shuzo Co., Ltd.) and KpnI (Takara Shuzo Co., Ltd.) and then ligated to pMAT137-Hm using DNA Ligation Kit Ver. 2 (Takara Shuzo Co., Ltd.). This plasmid (referred to hereinafter as "pMAT137-Hm+CPC") was introduced into $E.$ $coli$ JM109 (Takara Shuzo Co., Ltd.) using Gene Pulser (BioRad), and the transformed $E.$ $coli$ was screened in an LB medium (1% Bacto-trypton, 0.5% Bacto-yeast extract, 1% NaCl, 1.2% agar powder) containing 50 mg/l hygromycin B (Wako Pure Chemistry Industries, Ltd.).

The plasmid was extracted from the transformed $E.$ $coli$ in DNA automatic separator P1100Σ (Kurabo Industries Ltd.). This plasmid pMAT137-Hm+CPC was introduced into Agrobacterium tumefaciens C58C1Rif using Gene Pulser (BioRad).

The Agrobacterium was cultured in an LB medium under shaking and transformed into the WS strain of Arabidopsis (scientific name: Arabidopsis thaliana) in the vacuum infiltration method (Bechtold, N et al., C. R. Acad. Sci. Paris, Life Science 316, 1194–1199 (1993)). The transformed plant was planted in culture soil and its seeds were harvested and screened for a drug resistant recombinant in a hygromycin-containing medium (mixed salt for 1×Ganborg B5 medium (Wako Pure Chemical Industries, Ltd.), 1% sucrose, 0.8% agar powder, 10 mg/ml hygromycin B (Wako Pure Chemical Industries, Ltd.). As a result, two transformants were obtained. These plants were planted and grown in culture soil, and their seeds were harvested.

Figure 4A:
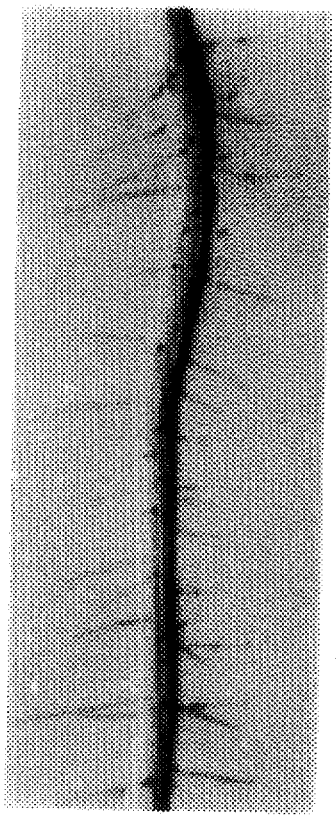
FIG. 4A is a photograph of a root of a plant overexpressing the CPC gene.
Figure 4B:
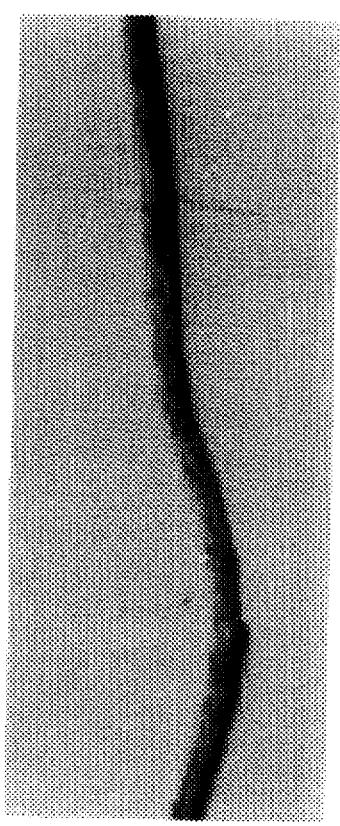
FIG. 4B is a photograph of a root of a plant overexpressing the CPC gene.
Figure 4C:
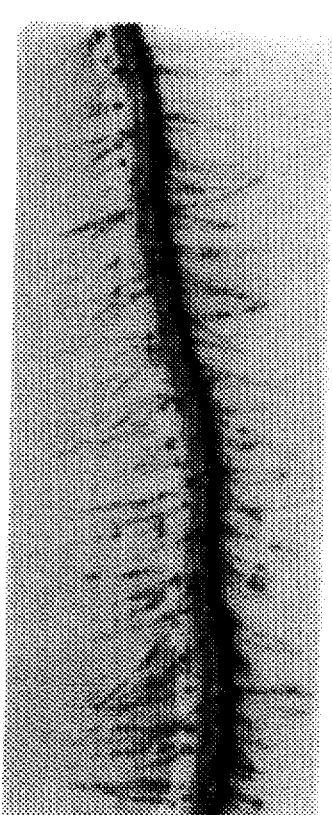
FIG. 4C is a photograph of a root of a plant overexpressing the CPC gene.

Plants from the harvested seeds having plasmid pMAT137-Hm+CPC inserted into their genome were examined for the number of their hair roots (number of hair roots/1 mm root). The determination of hair roots was made by examination under a stereoscopic microscope and 20 plants were examined for each line. The average number of hair roots±standard error is shown in Table 1. A photograph of roots of Arabidopsis under a stereoscopic microscope is shown in FIG. 4A–C. In FIG. 4A–C, "A" shows the wild-type; "B", mutant "caprice"; and "C", the plant with excessive expression of the CPC gene.

TABLE 1

| Strain | Number of Root Hairs (number/mm) |
|---|---|
| wild-type | 43.2 ± 1.0 |
| mutant "caprice" | 10.6 ± 0.6 |
| mutant "gl2" | 111.8 ± 6.2 |
| mutant "ttg" | 98.2 ± 3.8 |
| double mutant "gl2 caprice" | 100.4 ± 2.4 |
| double mutant "ttg caprice" | 65.2 ± 2.6 |
| plant #1 with excessive expression of CPC gene | 135.2 ± 4.8 |
| plant #2 with excessive expression of CPC gene | 102.4 ± 3.2 |

As shown in Table 1, the root hairs of the planta having plasmid pMAT137-Hm+CPC inserted into their genome are 2- or 3-times as much as those of the wild-type (plants #1 and #2 have 3.1- and 2.3-times root hairs as much as the wild-type respectively). That is, the number of root hairs is increased with excessive expression of the CPC gene in Arabidopsis, while the number of root hairs is decreased in the mutant "caprice" with the CPC gene being destroyed.

Figure 5A:
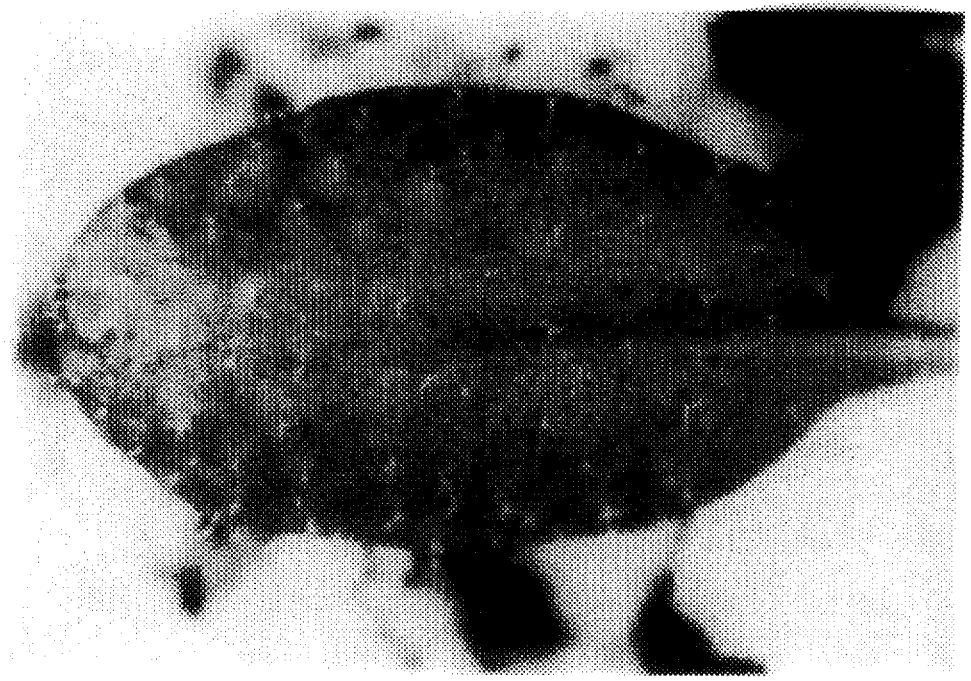
FIG. 5A is a photograph of a leaf of a plant overexpressing the CPC gene.
Figure 5B:
FIG. 5B is a photograph of a leaf of a plant overexpressing the CPC gene.
Figure 6A:
FIG. 6A is a photograph of a stem of a plant overexpressing the CPC gene.
Figure 6B:
FIG. 6B is a photograph of a stem of a plant overexpressing the CPC gene.
Figure 7A:
FIG. 7A is a photograph of wild type leaves.
Figure 7B:
FIG. 7B is a photograph of leaves of ttg.
Figure 7C:
FIG. 7C is a photograph of leaves of gl1.
Figure 7D:
FIG. 7D is a photograph of leaves of gl2.

There was a reduction in the number of trichomes in leaves and stems of the plants having pMAT137-Hm+CPC introduced into their genome. Trichomes are outgrowths from epidermal cells in leaves, stems etc. over the ground, and a trichome in a leaf is divided into 3 branches. FIGS. 5B and 6B show respectively a leaf and stem of the plant with excessive expression of the CPC gene. FIGS. 5A and 6A show respectively a leaf and stem of the wild type.

In summary, the plant with excessive expression of the CPC gene has an increased number of root hairs, while having a less number of hairs on its leaves and stems i.e. on the portion over the ground.

As other Arabidopsis mutants having an increased number of root hairs, ttg and gl2 were identified (Galaway et al., 1994; Massuci et al., 1996). These 2 mutants were originally separated as mutants on trichomes of leaves (Koorneef et al., 1982; Hulskamp et al., 1984, FIGS. 5A–B).

The phenotype of the plant with excessive expression of the CPC gene is the same as that of ttg and gl2 in respect of root hairs and trichomes.

Example 9
Construction of Double Mutants on Root Hairs

Caprice was crossed respectively with gl2 and ttg to give a double mutant as a cross between caprice and gl2 and a double mutant between caprice and ttg.

The phenotype for root hairs of the double mutant between caprice and gl2 was similar to that of gl2 (Table 1). This suggested that the CPC gene is located upstream of the gl2-related gene.

The phenotype for root hairs of the double mutant between caprice and ttg was an intermediate type between the 2 mutants (Table 1). This suggested that the CPC gene and the ttg-related gene interact with each other in some way to participate in the formation of root hairs.

What is claimed is:

1. A CPC gene coding for the amino acid sequence of SEQ ID NO:1 or an amino acid sequence substantially identical with the amino acid sequence of SEQ ID NO:1.

2. Plants having the CPC gene of claim 1.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 94 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:1:

```
Met Phe Arg Ser Asp Lys Ala Glu Lys Met Asp Lys Arg Arg Arg Arg
 1               5                  10                  15

Gln Ser Lys Ala Lys Ala Ser Cys Ser Glu Glu Val Ser Ser Ile Glu
            20                  25                  30

Trp Glu Ala Val Lys Met Ser Glu Glu Glu Glu Asp Leu Ile Ser Arg
        35                  40                  45

Met Tyr Lys Leu Val Gly Asp Arg Trp Glu Leu Ile Ala Gly Arg Ile
    50                  55                  60

Pro Gly Arg Thr Pro Glu Glu Ile Glu Arg Tyr Trp Leu Met Lys His
65                  70                  75                  80

Gly Val Val Phe Ala Asn Arg Arg Arg Asp Phe Phe Arg Lys
                85                  90
```

( 2 ) INFORMATION FOR SEQ ID NO:2:

( i ) SEQUENCE CHARACTERISTICS:
      ( A ) LENGTH: 282 base pairs
      ( B ) TYPE: nucleic acid
      ( C ) STRANDEDNESS: double
      ( D ) TOPOLOGY: linear ( i i ) MOLECULE TYPE: cDNA ( x i ) SEQUENCE DESCRIPTION: SEQ ID NO:2:

```
ATGTTTCGTT CAGACAAGGC GGAAAAAATG GATAAACGAC GACGGAGACA GAGCAAAGCC      60

AAGGCTTCTT GTTCCGAAGA GGTGAGTAGT ATCGAATGGG AAGCTGTGAA GATGTCAGAA     120

GAAGAAGAAG ATCTCATTTC TCGGATGTAT AAACTCGTTG GCGACAGGTG GGAGTTGATC     180

GCCGGAAGGA TCCCGGGACG GACGCCGGAG GAGATAGAGA GATATTGGCT TATGAAACAC     240

GGCGTCGTTT TTGCCAACAG ACGAAGAGAC TTTTTTAGGA AA                        282
```

( 2 ) INFORMATION FOR SEQ ID NO:3:

-continued (i) SEQUENCE CHARACTERISTICS:
  (A) LENGTH: 40 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:3:

CACGCCATCG ATGTAATAAT TGTCATTGTC ATTAGATTGT    40

(2) INFORMATION FOR SEQ ID NO:4:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:4:

GAGCTATTGG CACACGAAGA ATGGT    25